United States Patent [19]

Ash et al.

[11] 4,403,984
[45] Sep. 13, 1983

[54] SYSTEM FOR DEMAND-BASED ADMINSTRATION OF INSULIN

[75] Inventors: Stephen R. Ash, Lafayette, Ind.; Marvin P. Loeb, Chicago, Ill.

[73] Assignee: Biotek, Inc., Arlington Heights, Ill.

[21] Appl. No.: 218,710

[22] Filed: Dec. 22, 1980

Related U.S. Application Data

[63] Continuation-in-part of Ser. No. 107,965, Dec. 28, 1979, abandoned.

[51] Int. Cl.³ .................. A61B 5/00; G01N 27/26
[52] U.S. Cl. ........................... 604/50; 128/632; 604/66
[58] Field of Search ............ 128/632, 635, 656, 213, 128/214; 604/50, 66

[56] References Cited

U.S. PATENT DOCUMENTS 4,240,438  12/1980  Updike et al. ............... 128/635

OTHER PUBLICATIONS

Guyton et al., Develop. of Implant Electochem Glucose Sensor, Report from Path Dept. Harvard Med School.
Chang et al., Validation and Bioeng. Aspects of an Implantable Glucose Sensor, Trans. Soc. Artif. Int Organs, 1973.
Scientific Tables, Dist. by Geigy Pharmaceuticals, 7th Ed., Documenta Geigy, Ardsley, N.Y.

Primary Examiner—George F. Lesmes
Assistant Examiner—Nancy A. B. Swisher

[57] ABSTRACT

A system is disclosed for demand-based administration of insulin which utilizes a change in a physical property of a patient's body fluid as an indicator that a change in the body fluid glucose level has occurred and that an appropriate amount of insulin should be supplied to the patient. Body fluid osmolality or one of its colligative properties are particularly suitable for this purpose. A second sensor for measuring such properties as electrical conductivity may be added to detect changes in osmolality caused by such factors as dehydration. Insulin can be delivered to the patient from an extracorporeal source by means of a dual lumen catheter. One lumen of the catheter provides a passageway for the insulin dose and the other lumen provides a passageway through which a replaceable sensors can be introduced into or removed from the patient's body. In the alternative, the entire insulin administration system can be implanted into the patient.

9 Claims, 20 Drawing Figures

GLUCOSE TOLERANCE TEST

Fig. 3.

SYSTEM FOR DEMAND-BASED ADMINSTRATION OF INSULIN

CROSS REFERENCE TO RELATED APPLICATION

This application is a continuation-in-part of a copending U.S. patent application Ser. No. 107,965 filed on Dec. 28, 1979 now abandoned.

DESCRIPTION

Technical Field

This invention relates to means for ascertaining insulin demand of a patient based upon measurable changes of a body fluid physical property and to means for controlled administration of insulin.

BACKGROUND OF INVENTION

Diabetes mellitus is a disease characterized by hyperglycemia, polyuria, and wasting. Hyperglycemia is due to decreased utilization of glucose and also increased production of glucose.

The discovery of insulin in 1922 has made it possible to control the blood glucose level in diabetic patients, at least partially. This enhanced the well being and survival of diabetic patients; however, recent studies indicate that long term complications of diabetes such as blindness, heart failure, kidney failure, neuropathy and vascular disease are not completely obviated by insulin therapy. It has been suggested that the foregoing long term complications are due to one or more of the following reasons: (1) the control of glucose levels by periodic injection of insulin is imperfect and better glucose control is important, (2) the control of metabolic substances other than glucose is important and necessary for the management of the diabetic patient, and (3) the levels of hormones other than insulin also should be adjusted, i.e., the glucagon concentration should be reduced.

To improve the control of glucose levels, several methods have been suggested. Among such methods are the "close control" method whereby a patient is hospitalized with attendant frequent assays of blood sugars and frequent insulin injections (e.g., before each meal). To effect control, the individual or the clinical laboratory has to perform frequent blood sugar analyses on a regular basis.

A further extension of the aforementioned treatment by "close control" is the use of a continuous or constant rate infusion of insulin using an insulin dispenser for infusion of this hormone into the patient. With such a machine, the rate of insulin administration must be predetermined by a physician, and further requires the maintenance of a steady diet and a continued uniform sensitivity of the patient to insulin.

It has been proposed to use a sensor responsive to the patient's glucose level for regulating the rate of insulin administration by the aforementioned insulin dispenser. However, all glucose sensors proposed to date have been unstable in vivo when used for time periods in excess of several weeks and thus are not very practical. A variety of problems have been encountered with such sensors: (1) Sensors that rely on the oxidation of glucose (with glucose oxidase) exhibit stability problems due to the inherent instability or inactivation of such enzymes, (2) sensors relying on the direct oxidation of glucose (by means of electrodes) encounter undesirable polarization phenomena on the electrode surfaces, (3) the in vivo period of reliability of heretofore known implanted glucose sensors is shortened by fibrous or fibrinous encasement. This is so because all heretofore known glucose sensors are rate-dependent. That is, the glucose concentration in a patient's blood is indicated by the reaction rate of glucose at the sensor. Glucose in the blood must diffuse to the electrode or to the enzyme present in the sensor. For reliable sensor signal output, a constant mass transfer resistance of glucose to the sensing element must be maintained. Progressive fibrous or fibrinous encasement of the sensing element continuously alters such resistance and requires frequent recalibration of the sensor.

Accordingly, there exists a pressing need for a reliable means for administering insulin to a diabetic patient utilizing a stable implantable sensor.

SUMMARY OF THE INVENTION

It has now been discovered that the glucose level and insulin need of a patient can be reliably ascertained by measuring at substantially equilibrium conditions certain changes that have occurred in a physical property, i.e., a property not involving in its manifestation a chemical change, of a body fluid of the patient. The requisite amount of insulin for diabetes management dispensed in response to a signal generated by such measurement. Determination of body fluid osmolality is particularly suitable for this purpose. Typical body fluids whose physical properties can be monitored for this purpose are blood, peritoneal fluid, subcutaneous fluid, or the like.

According to the present invention, a system for administration of insulin responsive to a patient's insulin requirement includes an insulin dispenser adapted for infusion of insulin into the patient, a transducer means responsive to a physical property of a body fluid of the patient and generating a signal having a magnitude which is a function of the aforementioned physical property of the body fluid, and preferably a function of or proportional to osmolality of the body fluid; and a dispenser control means operably associated with the transducer means and with the insulin dispenser to receive the signal and to dispense insulin in response to the magnitude of the received signal. The insulin dispenser can be adapted for implantation, for iontophoresis, or for subcutaneous or transcutaneous infusion, as desired. Where the insulin dispenser is external to the patient's body, insulin delivery to the patient is effected via a cannula or by percutaneous catherization using a catheter made of a biocompatible material. Preferably the catheter also is provided with a barrier against infection.

In some cases it may be desirable to be able to measure the concentration of other blood constituents such as sodium or potassium levels. The concentration of such electrolytes can be determined by implanting a secondary transducer which can be designed to measure the conductivity or ion concentration of the blood fluid.

A preferred transducer means for the purpose of the present invention is an implantable blood or tissue fluid osmolality sensor or detector, e.g., an implantable osmometer that generates an electrical, mechanical or telemetry signal which, in turn, controls the operation of the insulin dispenser. Another embodiment would have a primary transducer sensing osmolality and one or more secondary transducers sensing electrolytic conductivity or ion concentration. A preferred insulin dispenser is a portable unit that can be worn by the patient or implanted in the patient, and includes an insulin reservoir, a pump means, and a switch means responsive to the signal or signals from one or more sensors or detectors and controlling the delivery of insulin.

In another preferred embodiment, an implanted sensor is used in conjunction with a dual channel catheter and has a shape enabling the sensor or sensors to be either (a) removed and replaced or (b) removed, cleaned of fibrinous or other material, and replaced through a channel in the catheter other than the channel carrying insulin to the patient.

Insulin from the reservoir can be delivered to the patient intraperitoneally, intravenously, or subcutaneously, or by any other convenient means as desired.

DESCRIPTION OF PREFERRED EMBODIMENTS

While the major effect of insulin in the mammalian body is the lowering of the blood sugar concentration, insulin can affect the concentration of a number of other body substances including potassium, phosphates, hydrogen, ketone bodies such as hydroxybutyrate and aceto acetate, fatty acid levels, sodium, and glycerol. In the diabetic state, the presence of many unidentified compounds is also noted, which compounds are not normal constituents of the body but which are believed to be metabolized by the body after insulin infusion. In the brain such "idiogenic osmols" can accumulate to levels of up to 40 milliosmols, and can cause cerebral edema or coma during treatment of diabetic ketoacidosis.

Osmolality is defined as the sum of the concentration of all solutes in a solution. Its units are "osmoles" or total moles of solute per kilogram of solvent. In the blood, the concentration of all chemical body substances is reflected by blood osmolality whether such substances can be chemically identified or not. It has been found that in the diabetic state, the effects of insulin infusion are reflected by a measurable change in blood osmolality and in osmolality of other body fluids. Moreover, it has been found that the detectable change in blood osmolality following exogenous and/or endogenous introduction of insulin has a greater absolute value than would be expected from the change in the blood glucose concentration. Changes in other substances such as fatty acids, glycerol, or "idiogenic osmols" are discernible by measurement of osmolality, even if such substances are not measured directly. Since the level of such substances is affected by the insulin level, variations in body insulin demand can be readily detected and accommodated so as to maintain blood osmolality within a desired range.

There may be some cases where it may be desirable to measure more than just the osmolality level. An increase in osmolality can sometimes be caused by severe physical exertion, dehydration or ingesting large amounts of certain electrolytes, e.g. table salt. While osmolality shows a good correlation with glucose levels, this correlation can sometimes be affected by these causes. Since a severely reduced level of water intake results in diminished water supply in both the intercellular and extracellular fluids, there is a resultant increase in the concentration of all metabolic substances. Such an increase can be detected by an increase in conductivity or ion concentration since the majority of extracellular osmoles are electrolytes. As the osmolality increases due to dehydration or ingestion of salt, the concentration of electrolytes increases raising the electrolytic conductivity and ion concentration. No large increase in electrolytic conductivity or ion concentration is caused by an increase in glucose or other substances controlled by insulin. By measuring the increase in conductivity or ion concentration in conjunction with the osmolality, e.g., by two separate sensing means, it is possible to "screen out" increases in osmolality not caused by increases in glucose and thus avoid an injection of insulin when it may be inappropriate. The outputs from the separate sensors may be subtracted from one another or otherwise processed, for example by using a microprocessor device so as to arrive at a control signal for dispensing insulin to the patient.

Figure 1:
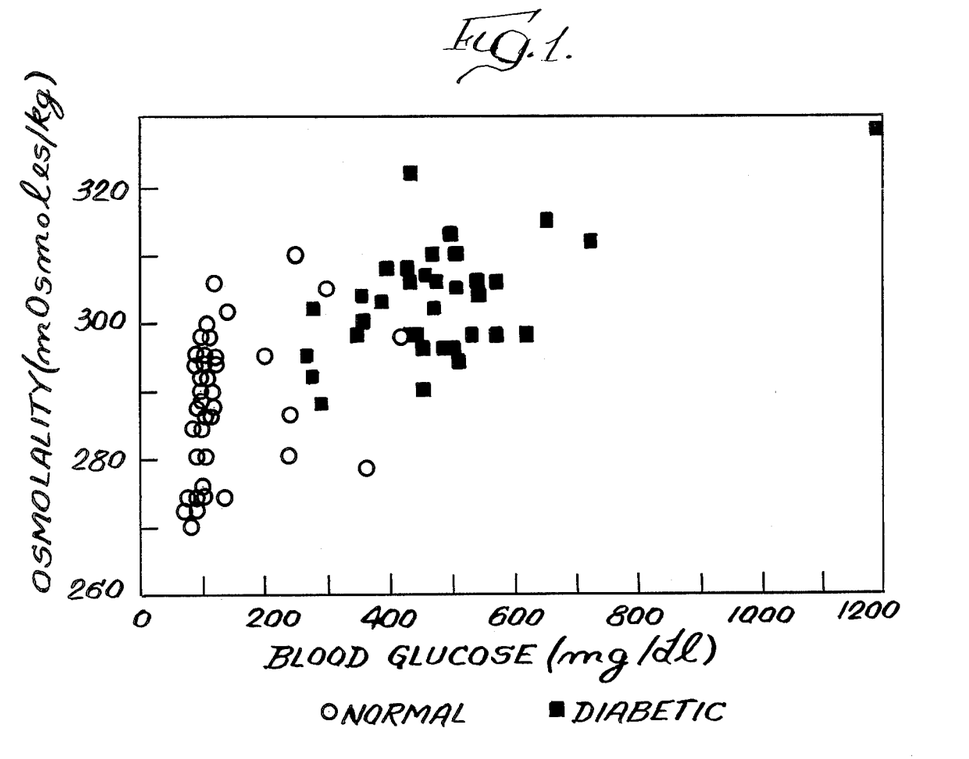
FIG. 1 is graphical correlation of blood glucose level and blood osmolality in normal and diabetic mammals.

FIG. 1 graphically illustrates the relationship between blood glucose concentration and blood osmolality in normal and in diabetic animals during loss of diabetic control over a time period of one day. Dogs were the experimental animals, and alloxan was used to induce diabetes. Intravenous glucose infusion was used to increase blood glucose levels. Insulin was omitted in the diabetic animal for 24 hours so as to induce loss of diabetic control. The data points were collected over a one day period and marked changes in osmolality occurred after the infusion of glucose. The slope of the early part of blood osmolality increase is relatively steep and thus provides a sensitive indication that an insulin infusion is needed.

In FIG. 1, it is seen that in a normal animal osmolality shows a weak relationship to blood glucose during the intravenous glucose infusion. Other solutes must be appearing or disappearing, to cause osmolar changes in the blood as opposed to glucose. In a diabetic animal, on the other hand, osmolality levels were already high, before glucose addition, and increased further in proportion to glucose levels between 200 and 400 mg%. The slope of increase is approximately 20 mOsm/kg per 200 mg% change in glucose concentration, approximately twice that predicted by the molecular weight of glucose alone. Accordingly, there are other solutes in the serum that contribute to this increase.

Figure 2:
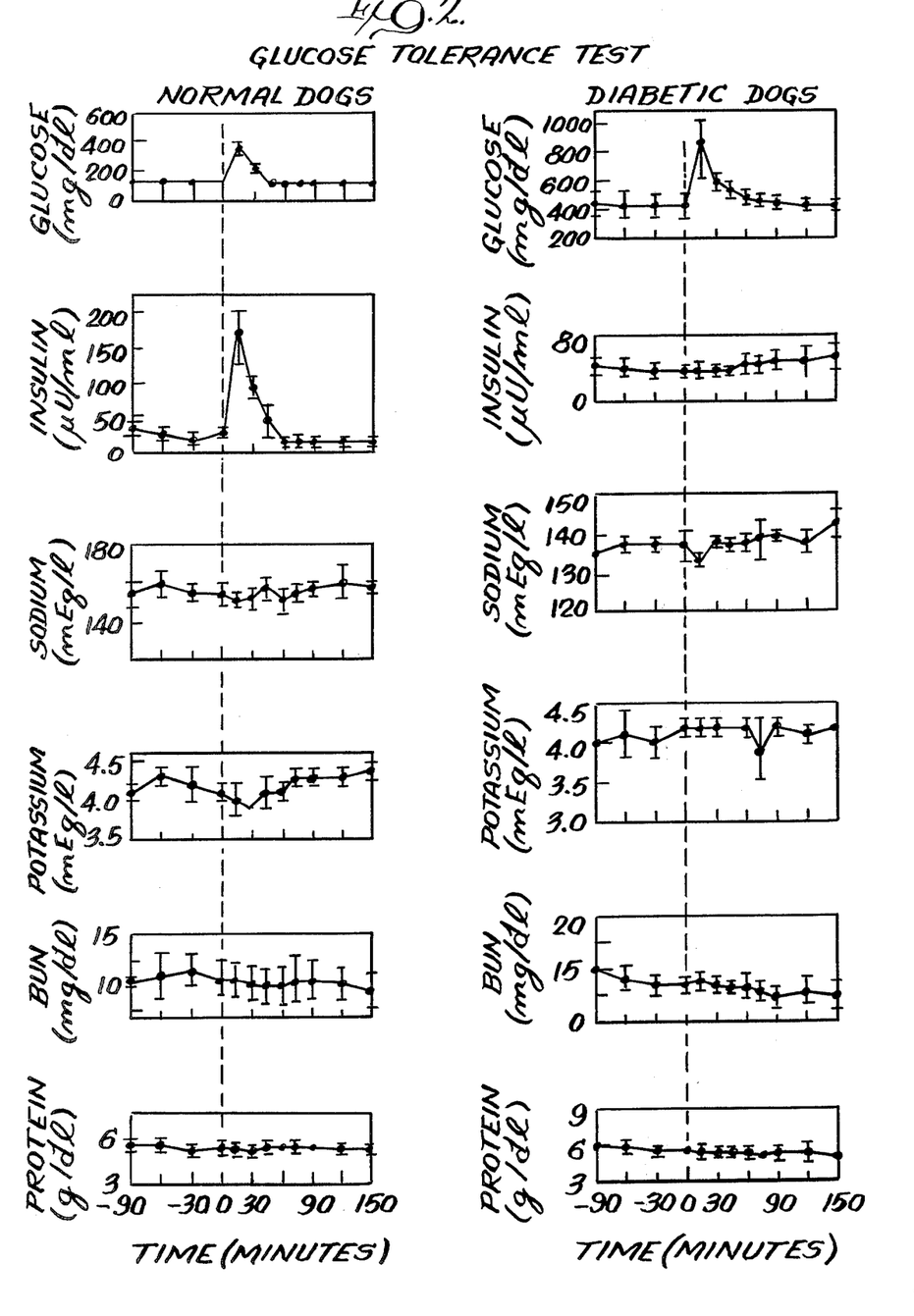
FIG. 2 is a graphical representation of the effect of endogenous insulin on various mammalian blood parameters.
Figure 2A:
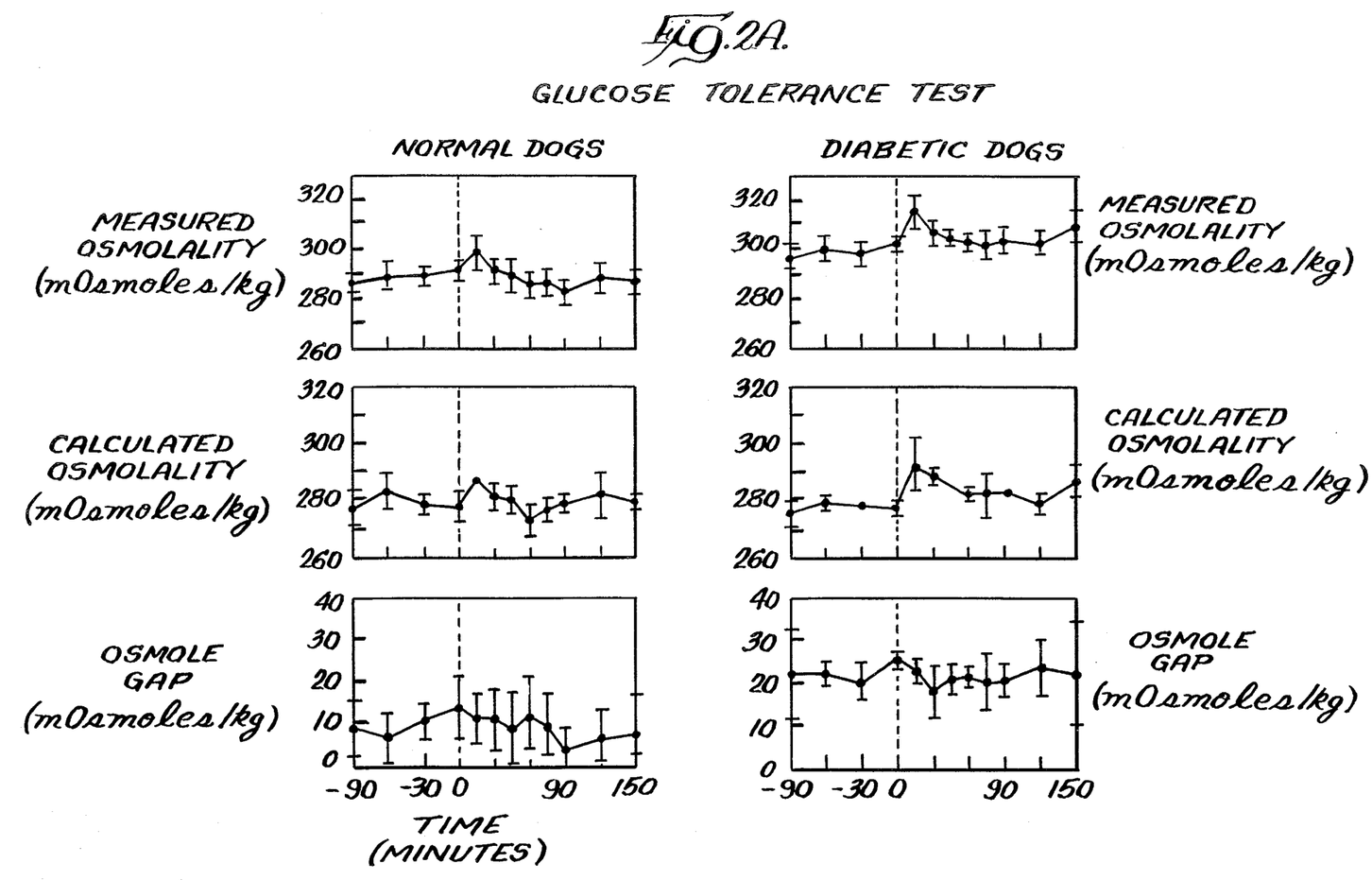
FIG. 2A is a graphical comparison of measured and calculated osmolality derived from the data shown in FIG. 2.

The time course of these osmolality changes is depicted in FIGS. 2 and 2A where various blood chemistries are depicted for one of the normal dogs. Samples were collected and insulin levels determined as set forth in the Example hereinbelow. Appropriate response of insulin to a glucose load is exhibited. It is seen that sodium, potassium, blood urea nitrogen (BUN) and protein change little during a glucose load, but that osmolality shifts dramatically, first increasing, then decreasing. The swings in osmolality are believed to be due to changes in "unmeasured" or "idiogenic" osmoles; these osmoles are indicated by the "osmol gap" calculated by subtracting out the effects of urea, Na, anions, and glucose from total osmolality. The osmolality changes are due to glucose and to other molecules, as yet unidentified. A decrease in osmolality to a level below normal is due in part to these unidentified molecules. In a normal animal, after a glucose level increase, the pancreas functions to return osmolality to normal.

Figure 3:
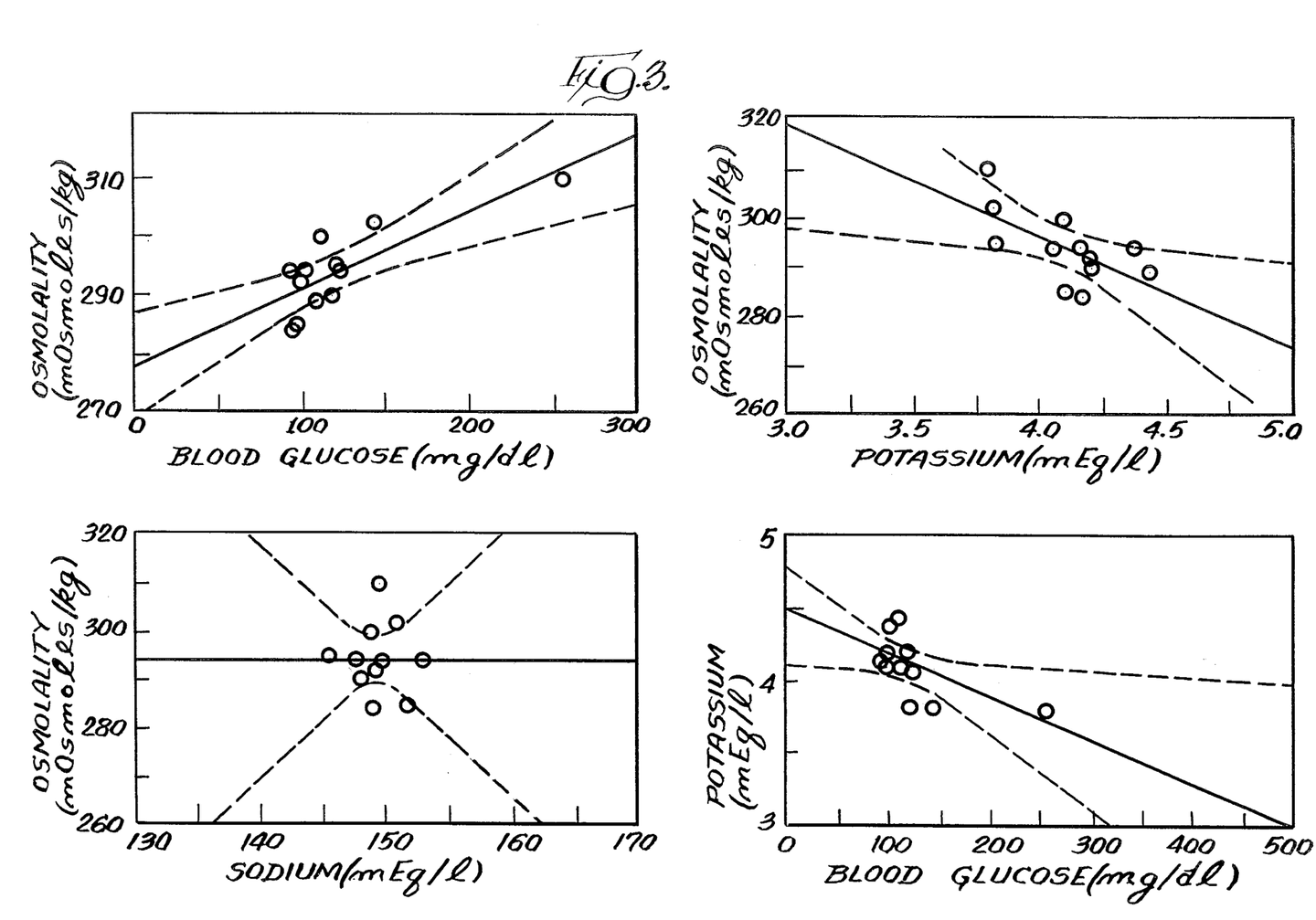
FIG. 3 is a graphical representation of the correlation of osmolality to glucose, Na, and K, in a typical normal mammal.

A sensor directly or indirectly responsive to osmolality changes in the body at a substantially equilibrium condition can be utilized to control the infusion of insulin and to minimize the adverse effects of diabetes. Such a sensor is sensitive to the degree of elevation of a number of important molecules besides glucose and a signal generated by the sensor controls insulin infusion, with resultant hypo-osmolality of the body stopping further dispensing of insulin. For implantation in a patient the sensor means should be compact and of relatively light weight, and preferably of a shape enabling removal through a catheter or cannula. As shown in FIGS. 1 and 3, osmolality is correlated with glucose, therefore control of osmolality also controls glucose.

Figure 4:
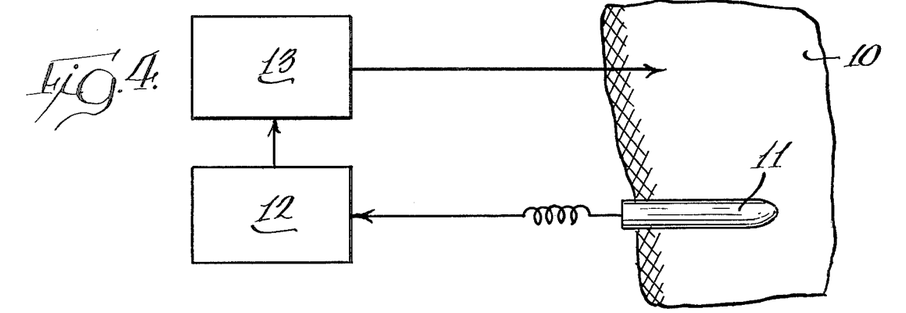
FIG. 4 is a block diagram showing a system for controlled administration of insulin that embodies the present invention.

FIG. 4 schematically illustrates a closed loop system for an effective diabetes control utilizing blood, osmolality for example, as the indicator of insulin demand. Osmolality of other body fluids is also suitable for this purpose. Transducer 11, such as an osmolality sensor, is introduced or implanted into patient 10 in any convenient manner, e.g., within patient's vascular space, subcutaneously, or intraperitoneally, so as to be in contact with a body fluid such as blood, subcutaneous blood, peritoneal fluid, or the like. This transducer means can also be applied to body surfaces, e.g., mucosal membranes, so as to be in contact with extracellular fluid, if desired. In any case, the magnitude of the signal generated by the transducer is a function of the osmolality of the body fluid in contact therewith and is utilized to control insulin infusion from reservoir 13 via a catheter, cannula, or similar means utilizing a control unit that receives the transducer signal by electrical or mechanical means, by telemetry, or in any other convenient manner as will be discussed in detail hereinbelow. Thus, a reliable indication of the patient's insulin demand is obtained and the demand can be satisfied by infusion of the desired amount of insulin with attendant control of a variety of metabolic sustances including glucose.

Osmolality alone or in conjunction with electrolytic conductivity or ion concentration may be measured in a variety of body fluids. There is rapid equilibrium between the intracellular, vascular, and interstitial components with respect to osmolality, electrolytic conductivity and ion concentration. The interstitial components are those fluids which are outside of cells and outside of the vasculature, and include peritoneal, subcutaneous, salivary, spinal fluids, and the like. A sensor for osmolality as well as for conductivity and ion concentration can be placed in contact with any of these.

The measurement of osmolality may be performed in several ways. There are four "colligative properties" of solutions, which change in proportion to osmolality: (1) vapor pressure, (2) oncotic pressure, (3) freezing point, and (4) boiling point. In each instance, the property measured is a function of the water concentration of the sample; water concentration decreases as solute concentration increases. Accordingly, preferably transducer 11 utilizes one or more of the aforementioned colligative properties to generate an output signal.

One of the most common methods of measurement of osmolality uses vapor pressure, defined as the pressure which water vapor exerts leaving the surface of a fluid. In a closed chamber, this pressure reaches equilibrium with the pressure of vapor in the gas above the fluid, and this pressure is proportional to the concentration of water in the vapor. This concentration of water may be measured conveniently by observation of the "dew point."

Figures 5, 6:
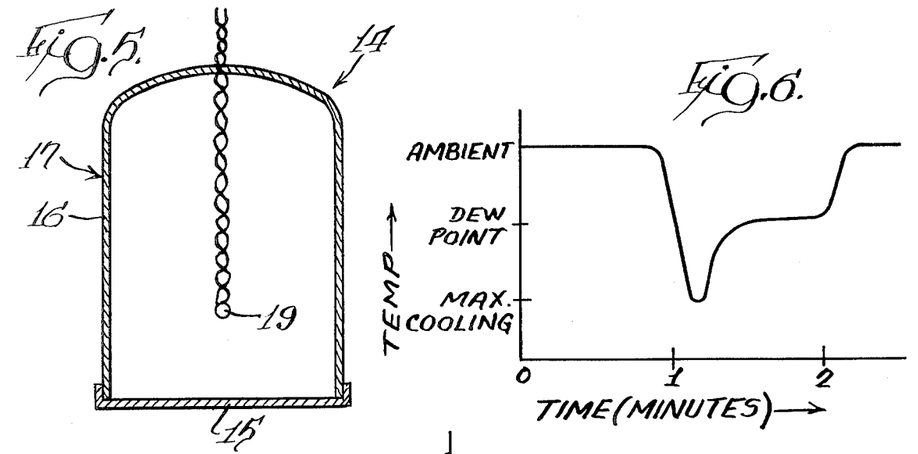
FIG. 5 is a schematic representation, partly in section, of a vapor pressure osmometer.
FIG. 6 indicates the thermocouple temperature curve for the osmometer shown in FIG. 5.

A typical instrument for this purpose is the Wescor Vapor Pressure Osmometer. An implantable osmometer 14 utilizing the same principle is schematically depicted in FIG. 5. In this particular osmometer, a body fluid permeable membrane 15, together with housing 16 define chamber 17. In the top portion of the chamber 17 is a very small thermocouple 19. When equilibrium of vapor pressure of the body fluid and gas is attained, the thermocouple is cooled several degrees by electric current (through the Peltier effect). The electric current is then stopped, and the temperature of the thermocouple rises to the "dew point" as water condenses on the thermocouple. A typical time-temperature relationship during this procedure is shown in FIG. 6. The "dew point" depression is the difference between ambient temperature and the dew point. As the vapor pressure decreases the dew point depression becomes larger. Lower vapor pressure indicates, of course, a lower concentration of water in the sample solution, that is, a higher concentration of solute (higher osmolality).

Vapor pressure determination of osmolality has been found to be exceedingly sensitive and generally reliable method for measuring liquid osmolality. Osmometer 14 can be calibrated against a known standard prior to implantation, and periodically after implantation by drawing an aliquot of the patient's blood and determining the osmolality thereof extracorporeally. Alternatively, a second osmometer, similar to osmometer 14 but with a hermeticallysealed chamber containing a known gas-water vapor mixture, can be implanted to serve as a periodic calibration means.

Oncotic pressure is another possible method for determination of osmolality. Oncotic pressure is defined as the pressure exerted across a semi-permeable membrane because of the presence of impermeable solutes. If a solute cannot pass through a membrane, its concentration is different on both sides of the membrane. There then exists a gradient of water concentration across the membrane. Because such membranes are usually permeable to water, there is a transfer of water across such a membrane. Such transfer will continue until pressure gradients occur to cause an equal transfer of water in the opposite direction.

Figure 7:
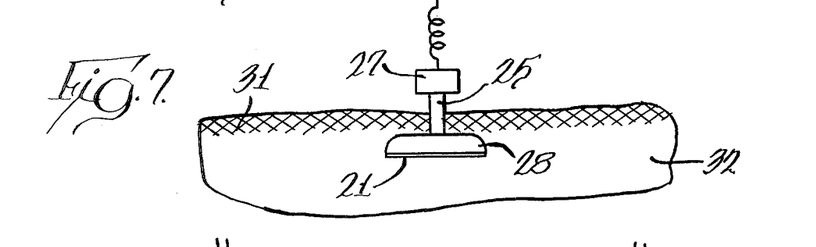
FIG. 7 is a schematic representation of an implantable oncotic pressure osmometer.

An osmolality sensor utilizing oncotic pressure is shown schematically in FIG. 7. A semi-permeable membrane 21, impermeable to certain solutes (such as glucose), is mounted on a rigid support 23 with a tube 25 leading to a pressure transducer 27 which can be piezoelectric gauge or the like. Semi-permeable membrane 21, made, for example, from polysulfone film, and support 23 are positioned under the patient's skin 31 embedded in subcutaneous tissue 32. The tube and support are filled with a solvent for body fluid constituents, such as water for example. Water moves across the membrane due to the concentration differences of solutes in water, and continues to move until pressure gradients on both sides of the membrane equilibrate. The pressure gradient existing at any given time is measured utilizing a pressure gauge or differential transducer. Such pressure is proportional to the concentration of non-permeant solutes (such as glucose and/or "unmeasured osmoles") in the body fluid in contact with membrane 21.

Figure 8:
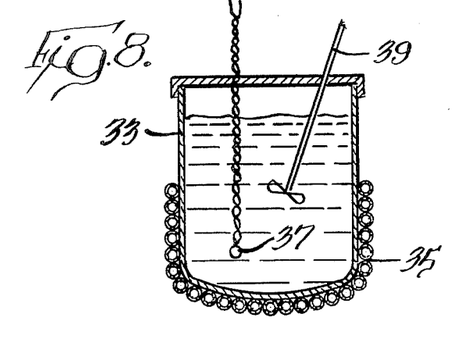
FIG. 8 is a schematic representation, partly in section, of a freezing point osmometer.

FIG. 8 schematically depicts a freezing point osmometer. Because of a variety of physical interactions of solutes with solvents, the freezing point of a solution decreases as its solute concentration increases. Thus, freezing point depression may be used to indicate osmolality of a solution. A body fluid sample is received in container 33 that is equipped with cooling coil 35. The sample is "super cooled," then made to freeze during agitation with stirrer 39. The temperature of solidification is determined using a thermocouple 37.

Figure 9:
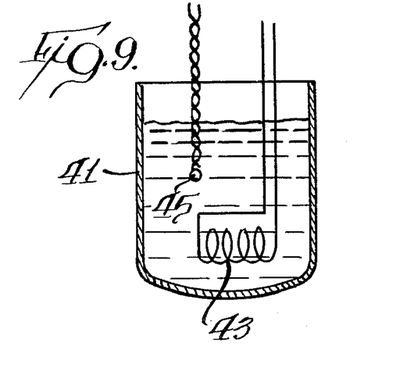
FIG. 9 is a schematic representation, partly in section, of a boiling point osmometer.

FIG. 9 depicts yet another possibility for osmotic pressure and thus osmolality measurement, that of boiling point elevation. The device comprises vessel 41 equipped with heating coil 43 and thermocouple 45. Since increasing solute concentration results in lower solvent concentration, boiling occurs at a higher temperature. The temperature at which a body fluid sample boils is measured with thermocouple 45, the temperature elevation being effected by heating coil 43.

The vapor pressure and oncotic pressure measurements in particular may be made easily and accurately by placing the sensor in various body fluids. One particular advantage is that water is extremely diffusable, and will allow rapid equilibrium within body fluids, such as the peritoneum. For bedfast patients the osmometer can be a separate, free-standing unit operably associated with an insulin dispensing device.

For any of these osmolality sensors, the generated signal is based on an equilibrium condition, i.e., the signal is not dependent on the rate at which a physical change takes place at the transducer, but rather on the equilibrium condition that is encountered. The problems encountered by prior art sensors, due to fibrous or fibrinous deposits on the sensor or transducer, are thus obviated or at least minimized and stable, accurate readings are obtained.

An increase in osmolality caused by dehydration or salt ingestion can also be detected by an electrolyte concentration increase by measuring electrolytic conductivity or ion concentration measurements. In the case of electrolytic conductivity, the measurement can be made by placing within the body biologically inert electrodes, such as platinum, in a fixed geometric relation and measuring the resistance value across the electrodes. Improved measurements can also be made by the application of alternating current at high frequency across the electrodes. 10,000–20,000 Hertz is a useful frequency for this purpose.

Electrolytic conductivity can also be measured by means of electrical induction without the use of contacting electrodes. Such measurements are made by inducing a current in the body fluid by use of a coil of wire. The magnitude of the induced current which can be measured by a second coil is proportional to the conductivity of the body fluid. Instead of or in addition to conductivity, it is also possible to measure the ion concentration of the fluid.

Ion concentration can be determined by measuring the electromotive force (voltage) between two electrodes placed in the body fluid where one of the electrodes is surrounded by a membrane chosen by one knowledgeable in the art according to the body fluid constituent wished to be measured. Such measurements could include total electrolytes, particular electrolytes such as potassium or sodium, pH, and disolved gases. In situations where there may be possible temperature variations, the measuring transducers could also include temperature compensators.

The osmolality, electrolytic conductivity and ion concentration sensors generate signals which are transmitted by means of an appropriate lead or leads, a radio signal, or similar expedients, to dispenser control means 12 which, in turn, energizes, or de-energizes, insulin dispenser 13, as indicated for transcutaneous delivery of the requisite dose of insulin. If a separate lead or leads to the sensor are used, the conductor portion of the lead can be coated with an inert, biocompatible sheath. Optionally, a fibrous cuff, e.g., a Dacron felt or the like, can be provided around the biocompatible sheath so as to form a barrier against infections. Dispenser control means 12 can be a micro-processor, a relay network, or any other switching means adapted to respond to the signal emitted by transducer means 11 and capable of energizing insulin dispenser 13. To the extent that fibrous or fibrinous deposits on a transducer may hinder the attainment of an equilibrium condition, control means 12 can include a delay means that permits energization of insulin dispenser 13 after a predetermined time period from the point in time when the signal from transducer means 11 is received. In this manner, consistent actuation of dispenser 13 can be assured as long as equilibrium can be attained at transducer means 11 within a predetermined time period. Alternatively, control means 12 can include a timing device that samples and compares signals received at predetermined intervals and energizes dispenser 13 only after differences among a plurality of received consecutive signals fall within a predetermined range.

Insulin dispenser 13 includes an insulin pool or reservoir and a pump means energizable from any convenient power source, e.g., a primary or secondary battery or gas propellant, in response to an output signal received from dispenser control 12.

Instead of an osmotic pressure measurement, the osmolality of the body fluid can also be determined using any other colligative property of the body fluid. For example, the transducer means can be adapted to measure freezing point depression, vapor pressure, or boiling point evaluation.

Likewise, control of the desired dose delivery of insulin can be effected based on electrical impedance measurements performed on the body fluid by means of implanted inert electrodes, e.g., platinum, and an alternating current generator. Electrical conductance measurements can also be used to obtain a signal suitable for controlling the infusion of insulin by means of dispenser 13.

In a method aspect of the present invention a body fluid of the patient is contacted with a transducer means that is responsive to a physical property of the body fluid, e.g., blood, which property is indicative of the patient's insulin deficiency, for example, osmolality or one of the colligative properties thereof such as vapor pressure or osmotic pressure. The transducer means is of the type that generates an output signal which is a function of the aforementioned physical property. The magnitude of the output signal generated as a consequence of the transducer means contacting the body fluid can then be utilized as an indicator of the patient's insulin requirement as well as to control the amount of insulin dispensed. Additional measurements of other body fluid properties such as electrolyte level, pH or dissolved gases by means of electrolytic conductivity or ion concentration measurements can be made, and the values thereof utilized in conjunction with the obtained osmolality value to provide a control signal to dispense the required amount of insulin. A microprocessor is well suited for this purpose.

The present invention is further illustrated by the following example.

EXAMPLE

Materials and Methods

Animals: Five mongrel dogs were used. Two were diabetic and three were non-diabetic. All dogs except one had a permanent indwelling catheter, the tip of which was in the cranial vena cava at the level of the second intercostal space. The canula exited from the jugular vein in the middle of the neck and was tunneled under the skin to the withers where it emerged. The free end was taped to a light harness which the dog wore all the time. One dog 17 had a temporary jugular catheter implanted before the IV glucose tolerance test.

Diabetes Induction: Diabetes was induced in two dogs (No. 17 and No. 22) with alloxan, 65 mg/kg. Dog No. 17 had been diabetic for 4 years. The other dog, No. 22, had been diabetic for 4 months. Insulin was withheld from the diabetic dogs on the day of the tests.

Glucose Tolerance Tests: Intravenous glucose tolerance tests were performed twice on each dog with the exception of the dog who had been diabetic for 4 years. Four fasting heparinized blood samples were drawn at 30 minute intervals to establish baseline values. A bolus of 50% glucose (2 ml/kg body weight) was injected via the catheter. Blood samples were drawn at 15 minute intervals for 90 minutes and then at 30 minute intervals for one hour. Diabetic dogs were not given insulin on the day of the glucose tolerance test.

Blood samples were centrifuged in a refrigerated centrifuge at 2000G's at 5° C. for 15 minutes. Plasma was removed, aliquoted for subsequent tests and frozen.

Blood glucose was measured by the glucose oxidase-periodase method, Boehringer Mannheim Corp., Catalog No. 124036. Insulin was measured using the Beckton Dickenson insulin assay kit, Catalog No. 231517. Insulin antibodies were removed from the plasma of diabetic dogs prior to insulin assay according to the method of Nakagawa et al., Diabetes 22:590–600 (1973). Osmolality was measured using the Wescor vapor pressure osmometer, Model No. 5130. Sodium and potassium were analyzed by flame photometry. BUN was analyzed on the Beckman BUN Analyzer II. Protein was determined using Folin Phenol reagent by the method of Lowrey et al., J. Biol. Chem. 193:265–275 (1951).

Data Analysis: The mean and standard error of the mean for each variable were calculated for each time period during the IV glucose tolerance test, for the normal and diabetic dogs. The data were normalized by setting the mean baseline value for each variable to zero in each test and calculating the difference between each observation and its corresponding mean baseline value. One-way analysis of variance was performed on each of the normalized variables over time to determine significance. Student-Newman-Keuls tests were performed to make multiple comparisons. A Student's t-test was used to compare the postinfusion osmole drop with baseline data. Forward least squares regression analysis was used to estimate the relationship of variables and to develop an equation for osmolality incorporating all measured variables. A stepwise regression analysis was used to pick the best set of variables to predict osmolality. A calculated value for osmolality was obtained using measurements of BUN, sodium and glucose by the formula provided by Edelman, J. S., Leibman, J., O'Meara, M. P., and Birkenfeld, L. W.: "Interrelationships between serum sodium concentration, serum osmolality and total exchangeable sodium, total exchangeable potassium and total body water." J. Clin. Invest. 37: 1236–1256, 1958:

$$\text{Osmolality} = 1.75\text{NA} + 0.0556\text{Glucose} + 0.357\text{BUN} + 10.1$$

The use of this value is discussed in further detail below.

Regression analyses of variance and Student-Newman-Keuls tests were performed on the Control Data Corporation's CDC 6500 computer using the Regression and One-way Programs of the Statistical Package for the Social Sciences (SPSS).

Results

Normal Dogs: FIG. 2 shows the variation in several blood parameters of one normal dog (No. 27), during an IV glucose tolerance test. During the 1½ hour baseline period the glucose, insulin, sodium, potassium, BUN and protein remained relatively constant. Osmolality varied within a 10 mOsmole range from 290 to 300 mOsmoles/kg. After glucose infusion, blood glucose rose from 118 to 352 mg/dl. Insulin rose from a mean baseline value of 4 μU/ml to 259 μU/ml in 15 minutes and returned to the baseline by 45 minutes. Osmolality rose from the mean baseline value of 295 mOsmoles/kg to 310 mOsmoles/kg in 15 minutes. Over the next 30 minutes the osmolality dropped by 25 mOsmoles/kg to 285 mOsmoles/kg.

In the aforementioned normal dog the correlation "r" between osmolality and blood glucose was 0.80 (FIG. 3). However, changes in blood glucose were not sufficient to explain the osmolality changes as the slope of this curve was greater than 1 mOsmole/180 mg/L. The sodium remained relatively constant during the entire test and showed no correlation with osmolality, $r=0.00$. Potassium changes were inversely proportional to both osmotic pressure ($r=0.64$) and glucose changes ($r=0.62$). BUN and protein levels remained relatively constant and showed little correlation with osmotic changes ($r=0.25$).

The mean values for the IV glucose tolerance tests on all of the dogs are illustrated in FIG. 2. During the baseline studies, the ranges in the measured variables for normal dogs were glucose: 105–110 mg/dl; osmolality 286–290 mOsmoles/kg; insulin: 17–32 μU/ml; sodium: 147–150 mEq/l; K: 4.1–4.4 mEq/l; BUN: 10–12 mg/dl; plasma protein: 5.4–5.9 g/dl. After intraveneous glucose administration, glucose rose to 230 mg/dl. This represents a 12.7 mOsmoles/kg contribution to osmolality. However, during this time the mean measured osmolality rose only 9 mOsmoles/kg, and then fell to 7 mOsmoles/kg below the mean baseline level.

The maximum decrease in measured osmolality for each dog occurred from 60 to 120 minutes after glucose administration and is therefore obscured in the mean data. The magnitude of the decrease ranged from 2 to 18 mOsmoles/kg below the baseline. The mean decrease is measured osmolality after intravenous administration of glucose was 10±3 mOsmoles/kg below baseline. A Student's t-test showed this drop to be significant at the $\alpha=0.05$ level: $t_{\alpha=0.5}{}^{3d.f.}=2.352$, calculated $t=2.94$. This decrease of osmolality below baseline cannot be explained by a drop in any specific solute below baseline levels.

Analysis of variance showed no significant differences over time in mean sodium, BUN, and protein levels after glucose infusion. The mean potassium level dropped slightly at 30 minutes, probably in response to the increase in insulin. The potassium level then rose and was significantly ($p=0.05$) higher from 120 to 150 minutes.

Diabetic Dogs: FIG. 1 also shows the variation in several blood parameters for one diabetic dog (No. 22) during an IV glucose tolerance test. During the 1½ hour baseline period the blood glucose fell spontaneously from 544 to 436 mg/dl; measured osmolality varied between 306 and 310 mOsmoles/kg; sodium rose from 126.1 to 138.0 mEq/l during the baseline period. Insulin, potassium and protein remained relatively constant both during the baseline period and after the infusion of glucose. After glucose infusion the blood glucose rose by 294 mg/dl. In 2½ hours glucose returned to the initial level of 440 mg/dl. After the glucose infusion, the measured osmolality rose only 5 mOsmoles/kg above the baseline value at 15 minutes. Osmolality continued to rise at 30 minutes to 315 mOsmoles/kg even as the glucose level was decreasing. The measured osmolality then fell to a minimum of 304 mOsmoles/kg at 60 minutes. It then rose to a maximum of 322 mOsmoles/kg at 2½ hours. Sodium decreased 3 mOsmoles after glucose infusion, returned to the zero time level by 90 minutes, and then decreased again.

In this particular test the correlation between blood glucose and osmolality was very low: $r=0.03$. The correlation between blood glucose and osmolality in other IV glucose tolerance tests on diabetic dogs were much higher: $r=0.95$ and $r=0.75$. In this test on dog No. 22 there was a slight correlation between sodium and osmolality ($r=0.24$). Osmolality was inversely proportional to potassium ($r=0.36$), BUN ($r=0.38$), and protein ($r=0.30$), however, these correlations are low.

The mean values of the measured plasma constituents of all diabetic animals during IV glucose tolerance tests are also shown in FIG. 2. Over the baseline period, the values were: glucose, 418–439 mg/dl; sodium, 134–137 mEq/l; potassium, 4.0–4.2 mEq/l; BUN 13–15 mg/dl; protein, 5.6–5.9 g/dl. The measured osmolality over the baseline period was 297–302 mOsmoles/kg.

After glucose infusion, in diabetic dogs the mean blood glucose rose to 810 mg/dl and returned to 424 mg/dl by 2½ hours. The insulin level remained relatively unchanged throughout the test. Sodium levels decreased to 133 mEq/l at 15 minutes and then increased above baseline levels reaching a maximum of 142 mEq/l at 2½ hours. Potassium levels remained within the baseline range except for a 3.9 mEq/l value at 75 minutes. BUN decreased slightly showing a minimum value of 12 mg/dl at 90 minutes. Protein also showed a slight tendency to decrease after glucose infusion, reaching a minimum value at 75 minutes.

The increase in blood glucose after glucose infusion represents a 21.2 mOsmoles/kg contribution to osmolality. However, the mean measured osmolality after glucose infusion rose only 16 mOsmoles/kg above the average baseline value. It then dropped to a minimum of 301 mOsmoles/kg at 75 minutes and subsequently rose again to 309 mOsmoles/kg at 150 minutes.

After the initial rise following glucose infusion osmolality did not decrease below the baseline value in the long-term diabetic dog (No. 17). In the other diabetic dog (No. 22) the decrease was 3–6 mOsmoles/kg below baseline between 60 and 75 minutes. This decrease is not significant, however ($p>0.05$).

In practicing the present invention, insulin can be infused as required utilizing a semi-permanently implanted percutaneous catheter, preferably of the type provided with a subcutaneously positioned fibrous cuff, made of polyester felt or similar material, that permits the ingrowth of tissue and capillary blood vessels therein. In this manner the catheter is not only fixed within the patient but also a barrier against bacterial invasion is effectively maintained.

Co-pending U.S. patent application Ser. No. 072,264, filed on Sept. 4, 1979, discloses an insulin infusion system that is suitable for continuous as well as intermittent delivery of insulin to the patient when used in conjunction with an osmolality sensor described hereinabove and is incorporated herein by reference to the extent pertinent.

The continuous infusion of insulin subcutaneously, intraperitonially or into a vein in response to a change in the physical property of a body fluid provides a more effective control of the patient's blood sugar level than is currently possible. Moreover, through the continuous infusion of insulin, the rate of insulin absorption is not influenced by such factors as exercise and temperature. In addition to the continuous delivery of insulin to the patient as controlled by transducer or sensor 11, the system shown in the aforementioned copending application permits the patient to elect to have an additional infusion (bolus) as required, for example, at or shortly before a meal.

The system includes a reservoir and a pump pack adapted to be strapped to the torso of a patient at an implanted catheter. The catheter is adapted to extend under the skin down the front of the chest with the tip near the entrance to the heart in a central vein.

This system includes a wearable pack including a one-piece prefilled insulin reservoir bag. When the insulin supply becomes exhausted and must be replaced, the pump segment (the heavy tube portion that is engaged by rollers in the pump) is removed by the roller section of the pump and the pump segment of a new supply is threaded through the pump thereby eliminating the pump as a contaminant to the system.

The delivery from the pump is controlled by a microprocessor programmed to respond to an input or inputs from the implanted osmolality sensor and possibly secondary sensors and is also designed to permit the patient to anticipate the need for an extra quantity (bolus) of insulin. In the latter instance a push-button control on the side of the wearable pack can be actuated for the bolus infusion. The microprocessor can also be programmed to prevent the patient from activating the bolus injection more than a predetermined number of times a day, depending upon the physician's prescription which can be preset in the microprocessor.

In another system embodying the present invention a reservoir and pump pack are adapted to be strapped to the torso of the patient. A dual channel catheter is adapted to extend under the skin (subcutaneously) down under the chest with the tip of the catheter near the entrance of a central vein. Other methods of vascular access may be employed depending on the requirements of the patient. Likewise, subcutaneous or peritoneal infusion of insulin may be effected. The catheter carries a cuff or sleeve of "Dacron" or other material into which the patient's tissue and blood vessels grow for permanent implantation, thereby reducing or obviating the possibility of bacterial infection.

The catheter itself is designed for prolonged implantation and can be constructed of a flexible silicone rubber (Silastic) or other physiologically compatible material having two parallel channels therethrough. One of these channels is the insulin infusion channel that is externally connected to the insulin pump. The other channel receives a lead wire or wires for the osmolality sensor and possible secondary sensors which project from and are positioned by the distal end of the sensor channel.

An important aspect of the present invention is that the dual channel catheter permits the removal and replacement (or removal, cleaning and replacement) of the osmolality sensor and any secondary sensor without the removal of the catheter itself. Because of fibrous or fibrinous deposits or the general degradation of the transducer means or sensors after a prolonged period of use it is necessary that they be periodically replaced or cleaned to prevent it adversely affecting the insulin delivery function. Toward this end, the external end of the catheter is split defining an insulin tube connectable to the insulin pump and a sensor tube having a releasable and removable cap through which sensor lead wires project. This cap has a conical projection that fits in and over and seals the end of the sensor tube. The cap also has a central bore therethrough that sealingly receives the sensor lead wires.

After a certain period of use, for example six months, a sensor can be replaced or cleaned, if desired, by removing the cap and withdrawing the sensor through the sensor channel and thereafter replacing the cleaned sensor or replacing it with a new sensor and cap. The position of the cap on the sensor lead wire determines the extent of projection and positioning of the sensor itself from the distal end of the sensor channel.

Figure 10:
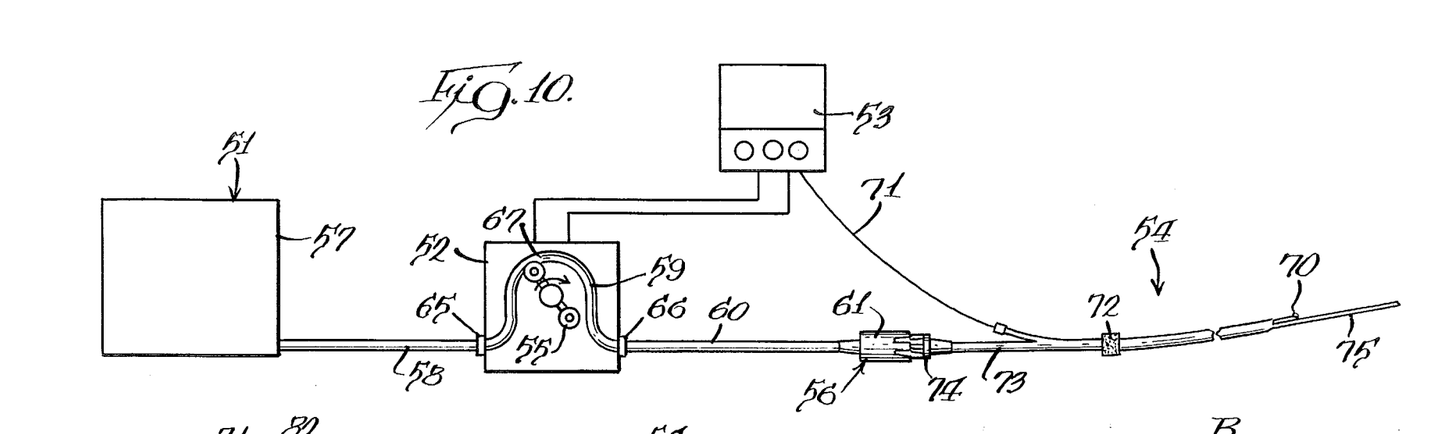
FIG. 10 is a schematic view of one embodiment of the present insulin infusion system including a supply reservoir, a micropump controlled by a microprocessor, and a dual channel catheter assembly for delivering insulin to the patient and providing signals to the microprocessor representing glucose levels in the patient.

Referring to FIG. 10, the insulin infusion system utilizing a dual lumen (channel) catheter is seen to include a replaceable insulin supply 51, small roller pump 52 controlled by a microprocessor 53 and an implanted catheter 54 connected to the insulin supply 51 through a releasable connector assembly 56. In lieu of pump 52 other types of small pumps can be used, for example a piezoelectric micropump of the general type shown in U.S. Pat. No. 3,963,380 and the like. The connector assembly 56 may take the form of the connector assembly disclosed in the aforementioned co-pending U.S. patent application Ser. No. 072,264 filed on Sept. 4, 1979, the detailed description of which is incorporated herein by reference to the extent pertinent.

While not shown in FIG. 10, the insulin supply 51, small pump 52, and microprocessor 53 can be assembled into a single pack adapted to be worn by the patient in any convenient manner, e.g., strapped to the torso, or, if sufficiently small, adapted for implantation.

Insulin supply 51 is a one piece plastic insert and includes a polyethylene insulin reservoir bag 57, tube section 58, pump segment 59, and outlet tube 60 and supply connector 61, the latter forming part of the connector assembly 56. The pump segment 59 of the insulin supply can be a segment of tube section 58 or a relatively heavy-walled section 67 terminating in pump blocks 65 and 66. Heavy walled section 67 is adapted to be engaged by the rollers 55 of the micropump 52. When the insulin supply 51 is replaced, the patient discards the exhausted supply unit, threads the pump section 59 of a new supply through the pump 52, and connects connector 61 to the connector assembly 56.

The pump 52 can be a relatively small roller pump. The microprocessor 51 can be a digital logic system appropriately programmed for controlling the infusion rate of pump 52 in accordance with signals provided by osmolality sensor 70 carried intracorporeally by the catheter 54 and providing signals to the microprocessor through a lead wire 71. The details of the necessary logic in the microprocessor 53 are readily apparent to an electronics engineer of ordinary skill given the intended function so the detailed schematic therefor is not included in the drawings. Suffice it to say that the microprocessor 53 includes a variable pulse generator for driving stepper motor 61 associated with pump 52 at a variable rate. An input circuit in microprocessor 53 responsive to changes in signal levels in sensor lead wire 71 biases the variable pulse generator and will increase the pulse rate to the stepper motor 61 in response to increases in the insulin demand, e.g., glucose level as sensed by sensor 70 in the patient's circulatory system and decreases the pulse rate to the pump 52 in response to decreased insulin demand sensed by sensor 70. In this manner insulin infusion rate is increased as patient's osmolality and glucose levels increase, and insulin infusion rate is decreased in response to decreased osmolality and/or glucose levels in a substantially continuous manner throughout the day.

The microprocessor 51 can also be programmed to provide automatically a higher insulin infusion rate at predetermined time periods during a 24-hour cycle, or the microprocessor can be programmed to make and store a series of insulin demand determinations at predetermined intervals, to extrapolate therefrom an anticipated peak demand, and to control insulin infusion rate accordingly.

Figures 11, 12, 13, 14:
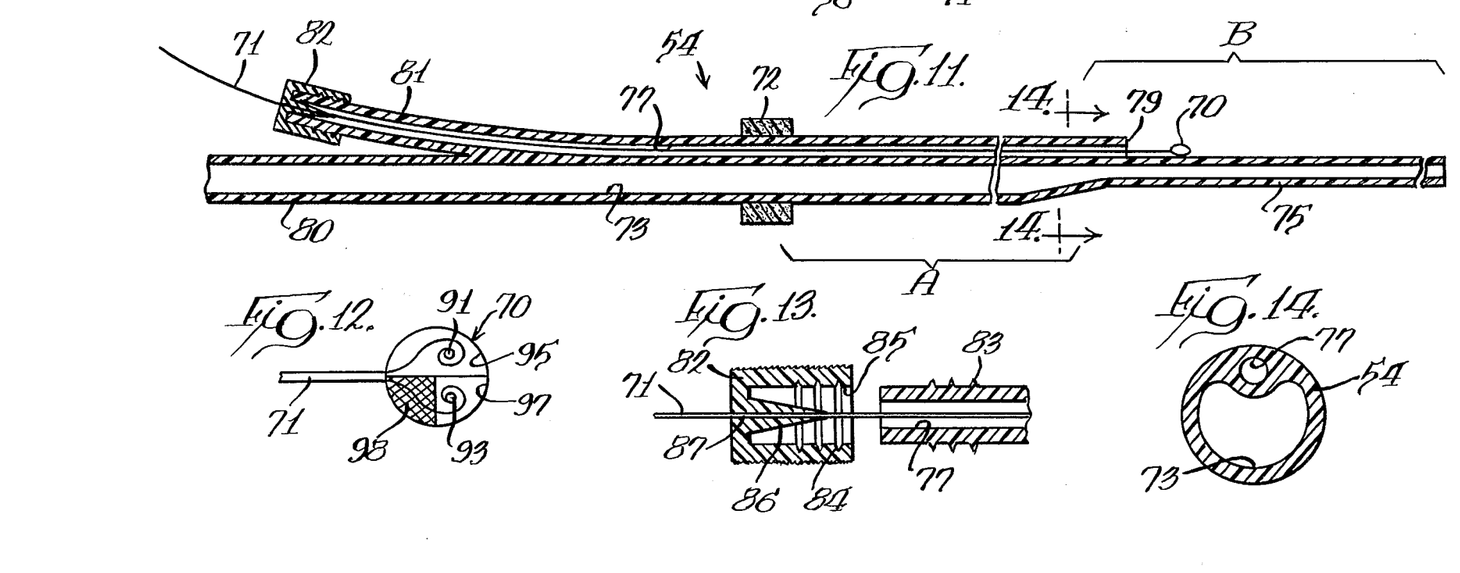
FIG. 11 is an enlarged cross-section of the catheter shown in FIG. 10.
FIG. 12 is an enlarged view of an exemplary replaceable sensor partly broken away to show interior detail.
FIG. 13 is an enlarged, exploded fragmentary section of the proximal end of sensor tube of the catheter and the replaceable cap therefor.
FIG. 14 is a cross-section taken generally along plane 14—14 of FIG. 11 showing the catheter sensor channel and insulin channel.

As seen in greater detail in FIG. 11, catheter 54 includes a left external section, an intermediate subcutaneous section A and an intraventricular section B. A tissue-impregnable cuff 72 surrounds the catheter 54 at the juncture of the external and subcutaneous sections to provide the catheter during prolonged implantation with an excellent bacteriological barrier. The catheter 54 includes an insulin passage 73 having a connector 74 at the end thereof adapted to be connected to connector 56 to receive insulin from pump 52. Passage 73 has a relatively narrow section 75 at its distal end that extends intravascularly.

The catheter also includes a smaller diameter sensor channel 77 that receives the replaceable sensor lead wire 71 and positions the sensor 70 adjacent its intravascular distal end 79. The distal end 79 of the catheter passage is spaced a considerable distance from the distal end of the insulin passage 75.

The external end of the catheter 54 is split, forming an insulin tube 80 and a sensor tube 81. A replaceable cap 82 is provided for the sensor tube 81 to seal the sensor and also to permit the removal and cleaning or removal and replacement of the sensor 53 periodically to prevent fibrous or fibrinous build up or other degradation of the sensor 70 from adversely affecting the response of the microprocessor 53.

As illustrated in FIG. 13, the proximal end of tube 81 has a plurality of annular integral projections 83 that hold and form a labyrinth seal with corresponding annular recesses 84 in the interior bore 85 of cap 82. To further seal sensor passage 77 from contamination, cap 82 has a narrow central opening 87 therethrough that sealingly receives lead wire 71 from sensor 70. The cap 82 is positioned on the lead wire 71 at a distance so that when the sensor is replaced, the sensor head 70 will be properly positioned the desired distance from the distal end 79 of the sensor passage 77 within the patient's blood vessel.

When periodic replacement of the sensor 70 is required, cap 82 is removed and the lead wire 71 withdrawn, withdrawing sensor 70 through sensor passage 77. A temporary cap may be attached to the catheter to prevent infection in the interior. Thereafter the cleaned sensor or a new sensor 70 is inserted, with the new cap 82, and the cap replaced connected to tube 81 and to the correct position of cap 82 on wire 71. The sensor 70 is then properly positioned.

The osmolality sensor 70 as shown in FIG. 12 is a vapor pressure osmometer of the type illustrated in FIG. 5 and comprises a pair of matched thermocouples 91 and 93 situated in respective chambers 95 and 97. Chamber 95 is a hermetically sealed enclosure containing water vapor in equilibrium with liquid water at body temperatures. Chamber 97 is substantially the same as chamber 95 but for the fact that a wall portion 98 thereof is made of a semi-permeable membrane such as polysulfone film, cellulose acetate film, or the like, so as to permit equilibration of water vapor pressure within chamber 97 with that of the surrounding body fluid. Standard dialysis membranes that prevent the passage of the relatively smaller solute molecules but that keep out proteins are also suitable for this purpose. To minimize accumulation within the chambers between measurements, the chambers can be pressurized to drive out the substances contained therein and to permit a new equilibrium to be established prior to making the next measurement. A sterile dry air or gaseous nitrogen sweep of the chambers can also be utilized for this purpose. Thermocouple 91 in chamber 95 provides a reference value for dew point of water at the body temperature existing at the time the osmolality measurement is made. For ascertaining sodium ion concentration in the body fluid, particularly suitable is a glucose-impermeable, sodium ion-permeable cellulose acetate membrane commercially available from Osmonics Corporation, Hopkins, Minnesota, under the designation Sepa-2.

Figures 15, 16, 17, 18:
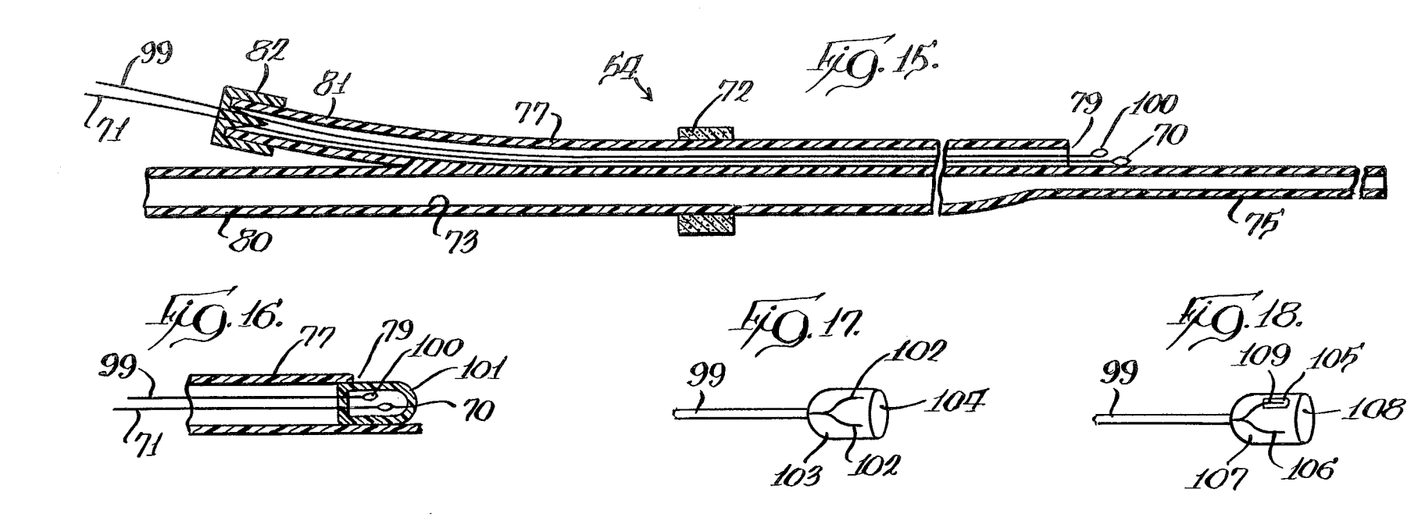
FIG. 15 is similar to FIG. 11, and is shown here to include a secondary sensor.
FIG. 16 shows the addition of a semipermeable membrane to encase the sensors.
FIG. 17 is an enlarged view of a conductivity sensor partly broken away to show interior detail.
FIG. 18 is an enlarged view of a ion concentration sensor partly broken away to show interior detail.

The use of two sensing transucers is shown in FIG. 15 which is a modification of FIG. 11. The osmolality sensor 70 and its lead 71 are as before, added are a secondary sensor 100 and its lead 99. The choice of this secondary sensor can be for conductivity or ion concentration.

The addition of semipermeable membrane capsule 101 which can be placed around the sensors shown in FIG. 16. This capsule can be attached to the sensors and be withdrawn with them. In a preferred embodiment the semipermeable membrane would be impermeable to bacteria but permeable to glucose and electrolytes and would form a seal about the distal end of the catheter 79, thus providing a second barrier against infection.

A cutaway view of the conductivity is shown in FIG. 17. The sensor has an open end 104 in the casing 103 and the two electrodes 102. Fluid enters the casing, and measurements are made by measuring resistance across the two electrodes.

In FIG. 18 is shown a cutaway view of an electromotive force detector with its casing 107, an open end 108, the exposed electrode 106, the sealed electrode 109 and the membrane 105. The membrane is chosen by one knowledgeable in the art depending on the body fluid constituent wished to be measured. This includes pH, total ion concentration or the concentration of particular ions such as potassium or sodium.

Figure 19:
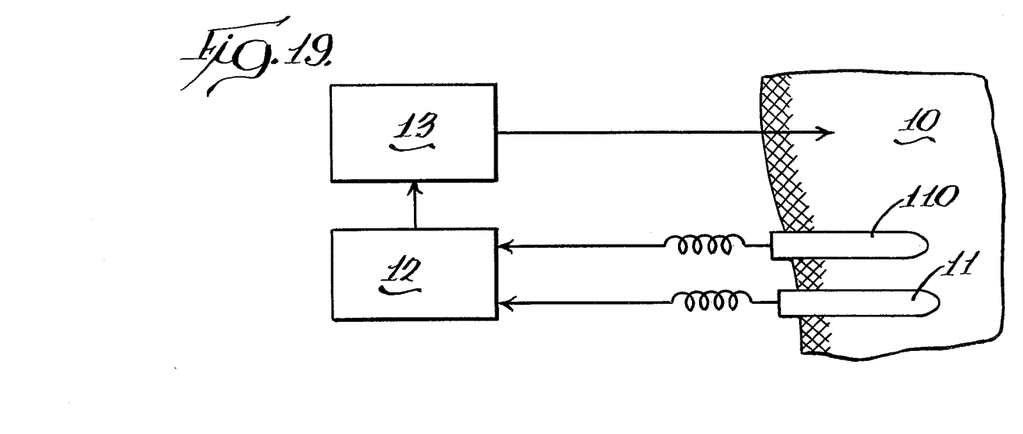
FIG. 19 is a block diagram showing a system for controlled administration of insulin using two sensors in the body.

FIG. 19 is a modification of FIG. 4 to show the use of a secondary transducer 110 placed in the body 10 to provide an additional input for the microprocessor 12 which controls delivery of insulin from the reservoir 13.

The foregoing discussion and the accompanying drawings are intended as illustrative, and are not to be taken as limiting. Still other variations and rearrangements of parts within the spirit and scope of the present invention are possible and will readily present themselves to one skilled in the art.

We claim:

1. The method for delivering insulin to a patient which comprises implanting into said patient, and in contact with a body fluid of said patient, a transducer means responsive to a physical property of said body fluid and generating an output signal which is a function of said physical property;

providing said patient with an insulin dispenser means adapted to deliver insulin transcutaneously to said patient;

providing a dispenser control means operably associated with said dispenser means so as to regulate delivery of insulin to said patient in response to a control signal; and applying the output signal generated by said transducer means to said dispensing control means as said control signal.

2. The method in accordance with claim 1 wherein said body fluid is a member of the group consisting of blood, peritoneal fluid, and subcutaneous fluid.

3. The method in accordance with claim 1 wherein said output signal is indicative of said body fluid osmolality.

4. The method in accordance with claim 1 wherein said physical property is oncotic pressure.

5. The method in accordance with claim 1 wherein the physical property is vapor pressure.

6. The method in accordance with claim 1 wherein the physical property is freezing point.

7. The method in accordance with claim 1 wherein the physical property is boiling point.

8. The method in accordance with claim 1 wherein said physical property is electrical impedance.

9. The method in accordance with claim 1 wherein said output signal is indicative of osmolality and including implanting a second transducer which generates a second output signal indicative of body dehydration and providing a dispenser control means operably associated with said dispenser means so as to regulate delivery of insulin to said patient in response to two control signals and applying the output signal indicative of osmolality and the second output signal as the two control signals.

* * * * *

UNITED STATES PATENT AND TRADEMARK OFFICE
CERTIFICATE OF CORRECTION

PATENT NO. : 4,403,984

DATED : September 13, 1983

INVENTOR(S) : Stephen R. Ash and Marvin P. Loeb

It is certified that error appears in the above-identified patent and that said Letters Patent is hereby corrected as shown below:

Col. 4, line 11, "hydroxybutyrate" should be -- β-hydroxybutyrate --.

Col. 6, line 3, "blood" (second occurrence) should be -- fluid --.

Col. 7, line 28, after "be" insert -- a --.

Col. 10, lines 51-52, "Osmolality=1.75NA+0.0556 Glucose+0.357BUN+10.1" should be -- Osmolality = 1.75 NA + 0.0556 Glucose + 0.357 BUN + 10.1 --.

Col. 11, line 37, "is" should be -- in --.

Col. 11, line 40, "$t_{\alpha=0.5}^{3d.f.}=2.352,$" should be -- $t_{\alpha=0.5}^{3d.f.} = 2.352,$ --.

Signed and Sealed this

Seventeenth Day of July 1984

[SEAL]

Attest:

GERALD J. MOSSINGHOFF

Attesting Officer

Commissioner of Patents and Trademarks